United States Patent
Kubo (10) Patent No.: US 9,775,493 B2
(45) Date of Patent: Oct. 3, 2017

(54) ENDOSCOPE, AND ENDOSCOPE SYSTEM PROVIDED WITH THE ENDOSCOPE

(71) Applicant: OLYMPUS CORPORATION, Tokyo (JP)

(72) Inventor: Takafumi Kubo, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/193,251

(22) Filed: Jun. 27, 2016

(65) Prior Publication Data

US 2016/0302651 A1    Oct. 20, 2016

Related U.S. Application Data

(63) Continuation of application No. PCT/JP2015/058031, filed on Mar. 18, 2015.

(30) Foreign Application Priority Data

Aug. 26, 2014   (JP) .................................. 2014-171967

(51) Int. Cl.
  *A61B 1/00*     (2006.01)
  *A61B 1/005*    (2006.01)
  (Continued)

(52) U.S. Cl.
  CPC .......... *A61B 1/00163* (2013.01); *A61B 1/005* (2013.01); *A61B 1/00009* (2013.01);
  (Continued)

(58) Field of Classification Search
  CPC ............ A61B 1/00163; A61B 1/00183; A61B 1/00096; A61B 1/015; A61B 1/05; A61B 1/00101; A61B 1/00009
  See application file for complete search history.

(56) References Cited

U.S. PATENT DOCUMENTS

2012/0116404 A1*  5/2012  Harp ................... A61B 1/00165
                                                  606/85
2012/0157773 A1*  6/2012  Honda ............... A61B 1/00096
                                                  600/164
(Continued)

FOREIGN PATENT DOCUMENTS

JP    H09-313435 A    12/1997
JP    2007-021161 A    2/2007
(Continued)

OTHER PUBLICATIONS

International Search Report dated Jun. 2, 2015 issued in PCT/JP2015/058031.

*Primary Examiner* — Timothy J Neal
(74) *Attorney, Agent, or Firm* — Scully, Scott, Murphy & Presser, P.C.

(57) ABSTRACT

An object of the invention is to provide an endoscope capable of continuously grasping a direction which a distal end portion of an endoscope faces even when a bending operation is performed. The endoscope of the invention is provided with: a first image pickup optical system provided at a distal end of an insertion portion; a bending portion provided in a vicinity of a distal end portion of the insertion portion and configured to be bendingly operated by a proximal side operation; and a second image pickup optical system disposed on the bending portion and configured so that the distal end of the insertion portion is included within a field-of-view angle.

10 Claims, 4 Drawing Sheets

(51) Int. Cl.
*A61B 1/015* (2006.01)
*A61B 1/018* (2006.01)
*A61B 1/05* (2006.01)
*G02B 23/24* (2006.01)
*A61B 1/04* (2006.01)

(52) U.S. Cl.
CPC ...... *A61B 1/00181* (2013.01); *A61B 1/00183* (2013.01); *A61B 1/015* (2013.01); *A61B 1/018* (2013.01); *A61B 1/05* (2013.01); *G02B 23/2423* (2013.01); *A61B 1/00096* (2013.01)

(56) References Cited

U.S. PATENT DOCUMENTS

| | | |
|---|---|---|
| 2012/0232345 A1 | 9/2012 | Levy et al. |
| 2013/0041214 A1* | 2/2013 | Maahs ............... A61B 1/00179 600/104 |
| 2014/0213850 A1 | 7/2014 | Levy et al. |

FOREIGN PATENT DOCUMENTS

| | | |
|---|---|---|
| JP | 2010-012079 A | 1/2010 |
| JP | 2013-141487 A | 7/2013 |

* cited by examiner

ENDOSCOPE, AND ENDOSCOPE SYSTEM PROVIDED WITH THE ENDOSCOPE

CROSS REFERENCE TO RELATED APPLICATION

This application is a continuation application of PCT/JP2015/058031 filed on Mar. 18, 2015 and claims benefit of Japanese Application No. 2014-171967 filed in Japan on Aug. 26, 2014, the entire contents of which are incorporated herein by this reference.

BACKGROUND OF THE INVENTION

1. Field of the Invention

The present invention relates to an endoscope provided with a plurality of image pickup units and capable of simultaneously observing a plurality of observation fields of view, and an endoscope system provided with the endoscope.

2. Description of the Related Art

Recently, an endoscope system has been widely used, in medical and industrial fields for example, which is configured with: an endoscope configured having an image pickup portion at a distal end part, having such a bending portion that a predetermined area near a distal end is configured to be bendable and that is bendingly operated by a proximal side operation, and having an insertion portion formed in an elongated tube shape as a whole, an image processing control apparatus configured to control the endoscope and the like and process image data acquired by the endoscope, an image display apparatus configured to receive the image data acquired by the endoscope and processed by the image processing control apparatus to display an image, and the like.

A medical endoscope used in the medical field is configured so that it is possible to insert the elongated insertion portion into a body cavity to be a subject, observe an organ in the body cavity and, when necessary, perform various kinds of treatments using a treatment instrument inserted in a treatment instrument insertion channel provided in the endoscope. Further, an industrial endoscope used in the industrial field is configured so that it is possible to, by inserting the elongated insertion portion into an inside of an object, for example, a jet engine or plant piping, perform observation and inspection of a state inside the object, for example, observation of scratches, corrosion and the like.

In a conventional endoscope in a form of this kind, it is difficult to, for example, at a time of inserting the insertion portion of the endoscope into a body cavity to be a subject, more specifically, into a large bowel or the like, grasp which direction the distal end part of the endoscope inserted in the body cavity faces, only by a front-view image pickup optical system of an image pickup portion disposed at a distal end face of the endoscope and configured to secure a forward field of view, and this causes the work of inserting the insertion portion of the endoscope to be difficult.

Therefore, various kinds of configurations have been disclosed and have been put to practical use, such as a configuration in which, by providing a side-view type second image pickup portion in addition to an ordinary front-view image pickup portion, at a distal end portion of an endoscope, forward and lateral fields of view can be simultaneously secured (Japanese Patent Application Laid-Open Publication No. H9-313435 and the like), and a configuration in which a front-view or oblique-view type second image pickup portion is disposed in a vicinity of a joint between a bending portion and a flexible tube (hose), in addition to, for example, an ordinary front-view image pickup portion at a distal end portion of an endoscope (Japanese Patent Application Laid-Open Publication No. 2013-141487 and the like).

By devising a configuration as described above, an advantage is obtained that it becomes easy to grasp a facing direction of a distal end part of an endoscope being inserted and used in a body cavity or the like and it becomes easy to perform an insertion operation.

SUMMARY OF THE INVENTION

An endoscope of an aspect of the present invention is provided with: a first image pickup optical system provided at a distal end of an insertion portion; a bending portion provided in a vicinity of a distal end portion of the insertion portion and configured to be bendingly operated by a proximal side operation; and a second image pickup optical system disposed on the bending portion and configured so that the distal end of the insertion portion is included within a field-of-view angle.

Further, an endoscope system of an aspect of the present invention is provided with: an endoscope provided with a first image pickup unit including a first image pickup optical system and a first image pickup device, the first image pickup unit being provided at a distal end of an insertion portion; a bending portion provided in a vicinity of a distal end portion of the insertion portion and configured to be bendingly operated by a proximal side operation; and a second image pickup unit disposed on the bending portion and including a second image pickup optical system configured so that the distal end of the insertion portion is included within a field-of-view angle and a second image pickup device; an image processing control apparatus configured to receive image signals from the first image pickup unit and the second image pickup unit and perform image processing, and control the whole system; and an image display apparatus configured to receive an image signal outputted from the image processing control apparatus and display an image.

DETAILED DESCRIPTION OF THE PREFERRED EMBODIMENTS

The present invention will be described below by embodiments shown in drawings. Each embodiment of the present invention illustrates an endoscope configured having an image pickup portion at a distal end part, having such a bending portion that a predetermined area near a distal end is configured to be bendable and that is bendingly operated by a proximal side operation, and having an insertion portion formed in an elongated tube shape as a whole, the endoscope being a medical endoscope to be inserted, for example, into a large bowel via an anus.

In each drawing used for description below, a different reduced scale may be used for each component so that the component is shown in a size recognizable on the drawing. Therefore, the present invention is not limited only to the number of components, shapes of the components, a ratio of sizes of the components and relative positional relationships among the respective components shown in the drawings.

First Embodiment

Figure 1:
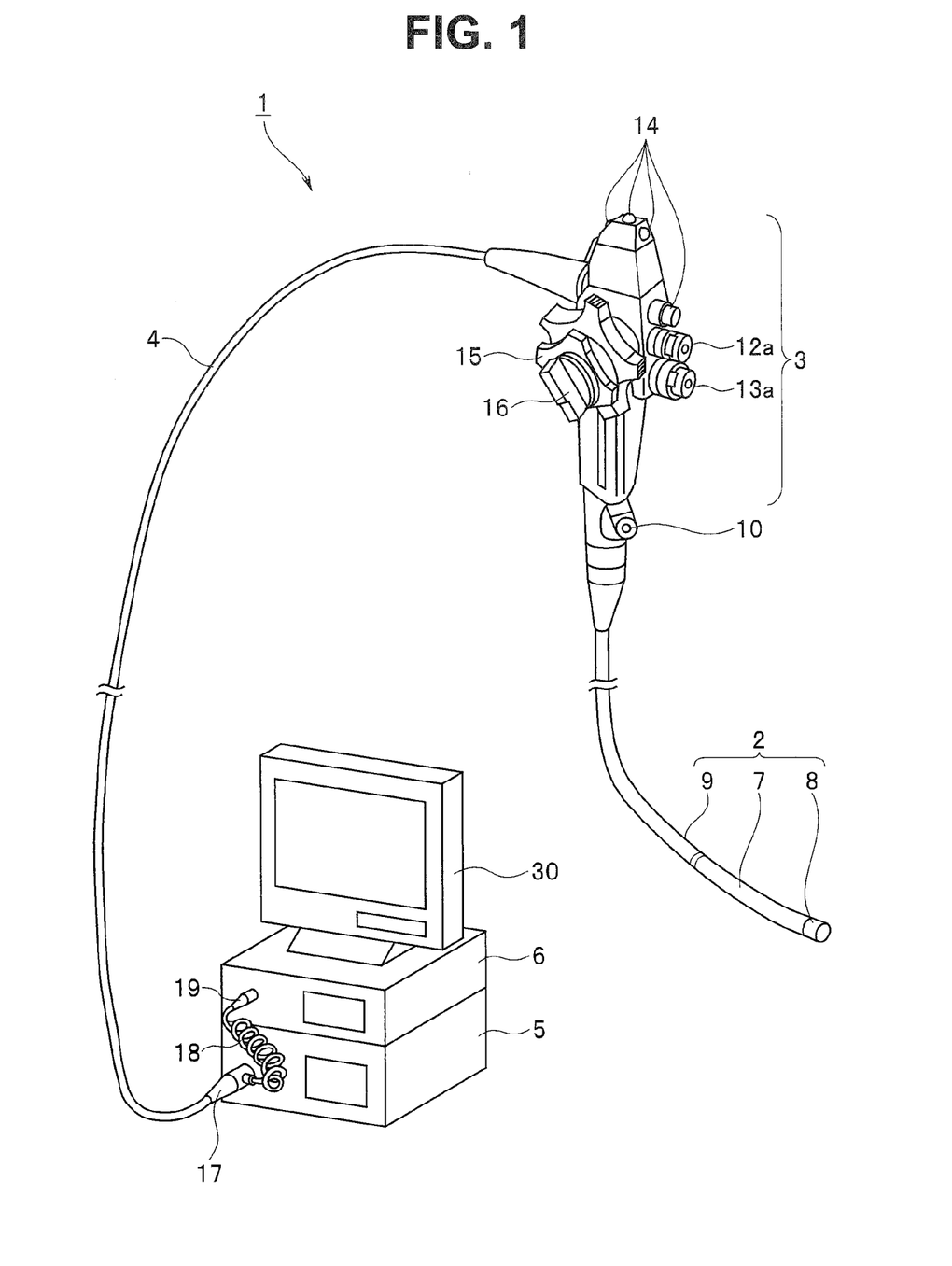
FIG. 1 is a schematic perspective view showing a main configuration of an endoscope system provided with an endoscope of a first embodiment of the present invention.
Figure 2:
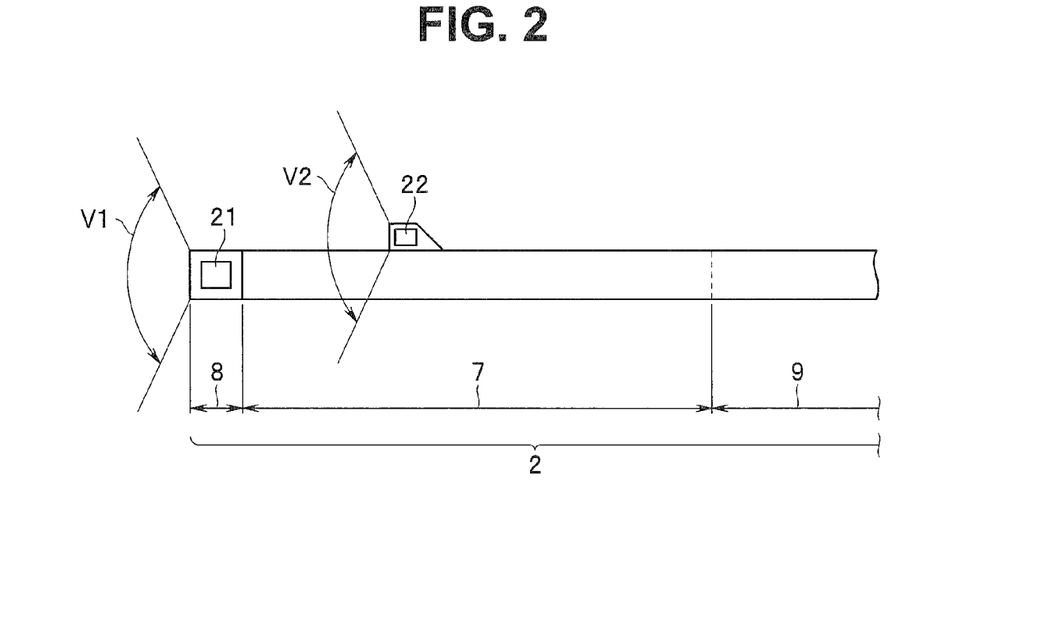
FIG. 2 is a conceptual diagram showing that a bending portion of the endoscope of the first embodiment of the present invention is in a non-bending state.
Figure 3:
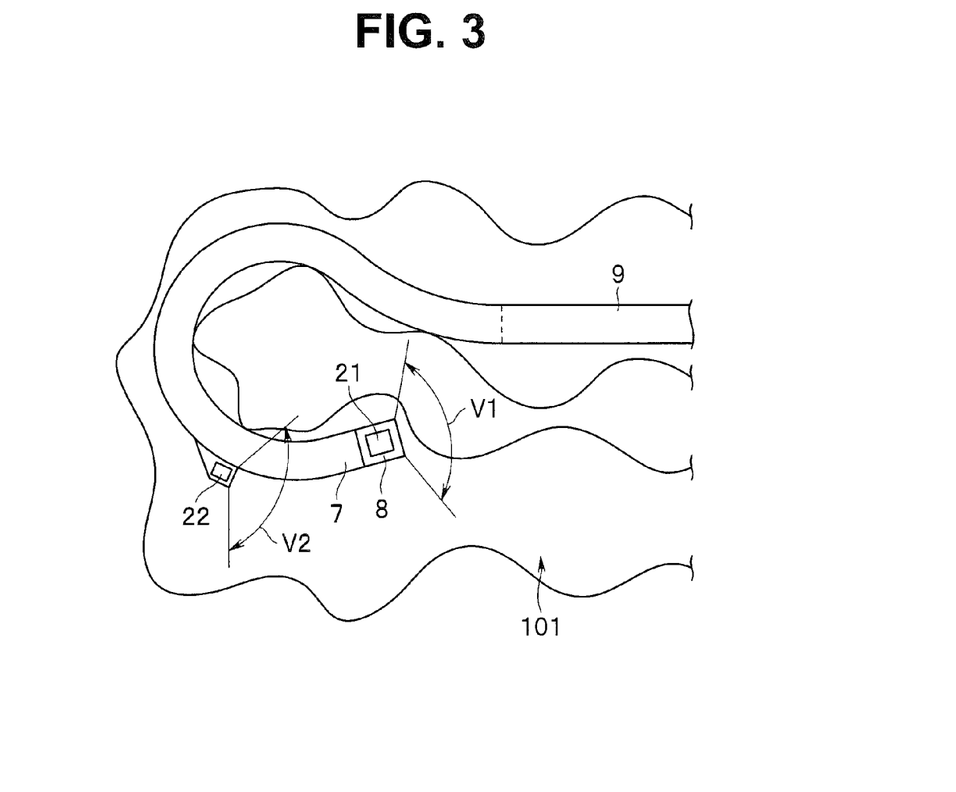
FIG. 3 is a conceptual diagram showing that the bending portion of the endoscope of the first embodiment of the present invention is in a bending state.
Figure 4:
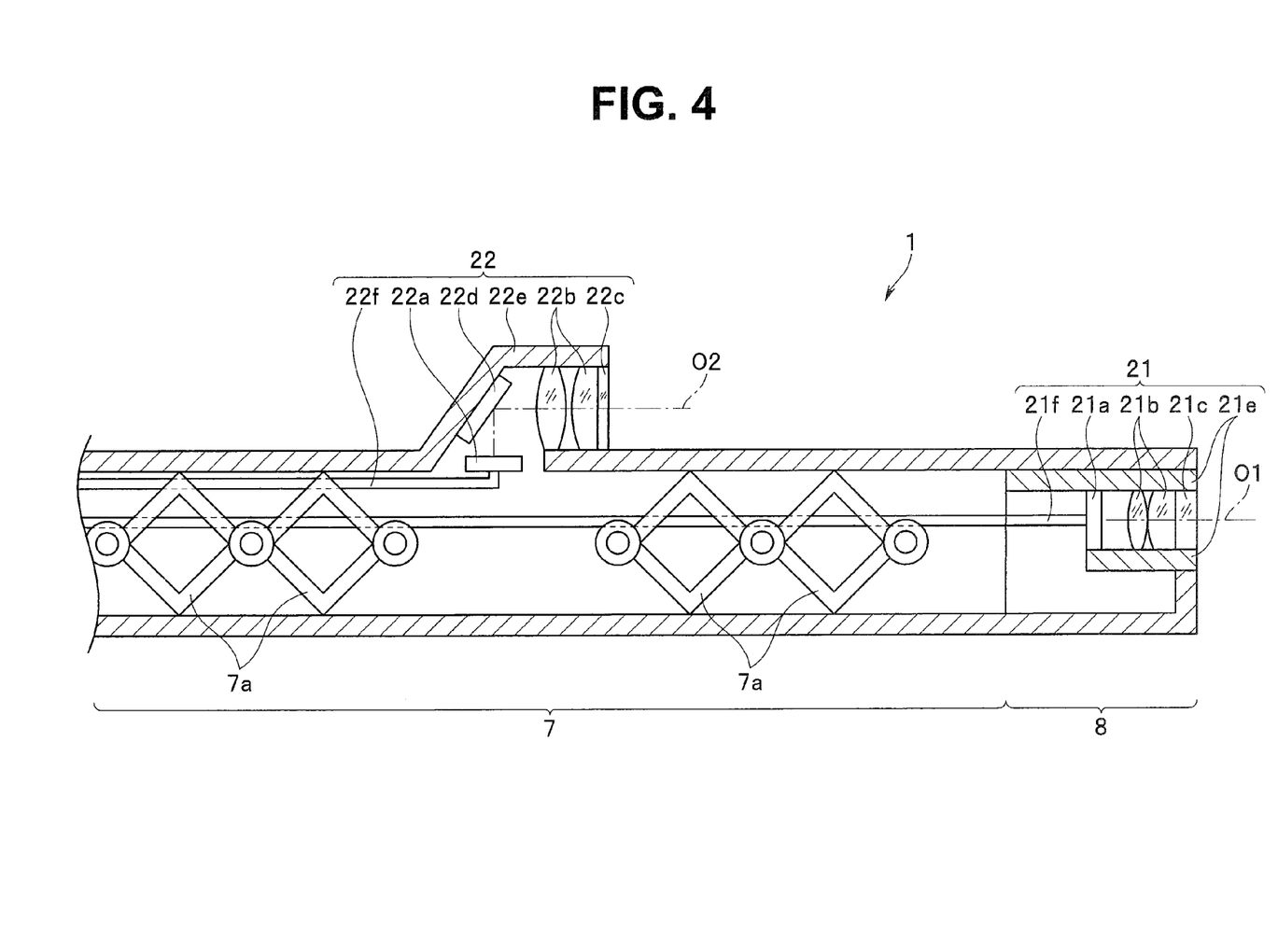
FIG. 4 is a vertical cross-sectional view showing an internal configuration in a vicinity of a distal end portion of the endoscope of the first embodiment of the present invention.

FIG. 1 is a schematic perspective view showing a main configuration of an endoscope system provided with an endoscope of a first embodiment of the present invention. FIGS. 2 and 3 are conceptual diagrams of the endoscope of the present embodiment. Between FIGS. 2 and 3, FIG. 2 conceptually shows that a bending portion of the endoscope is in a non-bending state. Further, FIG. 3 conceptually shows that the bending portion of the endoscope is in a bending state. FIG. 4 is a vertical cross-sectional view showing an internal configuration in a vicinity of a distal end portion of the endoscope of the present embodiment.

First, a schematic configuration of the endoscope system provided with the endoscope of the first embodiment of the present invention will be described below with use of FIG. 1.

As shown in FIG. 1, the endoscope system of the present embodiment is configured with an endoscope 1, a light source apparatus 5, a video processor 6 which is an image processing control apparatus, an image display apparatus 30 and the like, which are external apparatuses.

The endoscope 1 is configured with an insertion portion 2 formed in an elongated tube shape, an operation portion 3 to be grasped and operated by a user, a coupling cord 4 for connecting the operation portion 3, the light source apparatus 5 and the video processor 6, and the like.

The insertion portion 2 is configured with a distal end rigid portion 8 which internally accommodates a first image pickup unit 21 (not shown in FIG. 1; to be described in detail later; see FIGS. 2 to 4) and the like, a bending portion 7 which is bendably configured and provided with a second image pickup unit 22 (not shown in FIG. 1; to be described in detail later; see FIGS. 2 to 4) on an outer circumferential face, and a flexible tube 9 configured with an elongated tubular member as a whole, which are connectedly arranged in that order from a distal end side, and a proximal end side of the insertion portion 2 is coupled with the operation portion 3.

The flexible tube 9 of the insertion portion 2 described above is covered with resin, for example, polyurethane, and the bending portion 7 coupled on a distal end side of the flexible tube 9 is covered with a soft elastic body.

The bending portion 7 is a component portion configured with a bending mechanism configured by connectedly arranging a plurality of bending pieces (not shown in FIG. 1; see FIG. 4), provided in a vicinity of a distal end portion of the insertion portion 2 and bendingly operated by a proximal side operation. As for the configuration of the bending mechanism itself, a configuration similar to a configuration which has been conventionally put to practical use in existing endoscopes is applied.

The distal end rigid portion 8 includes the first image pickup unit 21 (see FIGS. 2 to 4) which is configured, for example, an image pickup optical system and an image pickup device and covers a forward field of view of the endoscope 1 as described above and, furthermore, includes an illumination optical system, air/water feeding nozzles and the like (not shown in FIG. 1). Further, the distal end rigid portion 8 is provided with one of openings of a forceps channel (not shown) made through the insertion portion 2. The other opening of the forceps channel (not shown) is disposed being connected to a forceps opening portion 10 provided on the operation portion 3.

The operation portion 3 is provided with a plurality of various kinds of operation members such as an operation member 12a for a suction conduit switching device to be operated at a time of performing suction, an operation member 13a for an air/water feeding conduits switching device to be operated at a time of performing air/water feeding, and a plurality of remote switches 14 for performing instruction operations for various kinds of signal processing for an image signal acquired by the first and second image pickup units 21 and 22 (to be described later) described above.

Furthermore, the operation portion 3 is provided with a plurality of angle knobs 15 made of hard resin. A configuration is made so that the bending portion 7 can be caused to bend in upward, downward, left and right directions by operating the (plurality of) angle knobs 15. On a top of the angle knobs 15, an operation member is provided, such as an engaging lever 16 made of hard resin and used when holding the bending portion 7 in a bending fixed state or releasing the bending fixed state.

The coupling cord 4 is covered with resin such as polyurethane, and a connector 17 formed with hard resin is attached to a distal end of the coupling cord 4. The connector 17 is provided with a connection cord 18 extended from a side face, a water feeding tube (not shown) to be connected to a water feeding tank (not shown) disposed inside the light source apparatus 5 to feed water, a suction port to be connected to a suction pump not shown to perform suction, and the like. Further, in addition to these, the coupling cord 4 is provided with an electrical contact, a light guide end portion and the like on a distal end side.

Thereby, a configuration is made so that, by connecting the connector 17 to a connector receiving portion of the light source apparatus 5, light emitted from the light source apparatus 5 is emitted forward from the illumination optical system (not shown) in the distal end rigid portion 8 via a light guide (not shown) disposed being inserted inside the endoscope 1.

Further, on a distal end side of the connector 17, an air feeding tube (not shown) is projectingly disposed substantially parallel to the light guide end portion (not shown). Therefore, a configuration is made so that, when the connector 17 is connected to the connector receiving portion of the light source apparatus 5, pressurized air from an air feeding pump (not shown) provided in the light source apparatus 5 is fed to the air feeding tube described above.

Furthermore, a distal end connector 19 of the connection cord 18 extending from the side face of the connector 17 is connected to a connector receiving portion of the video processor 6. Thereby, an electrical image signal outputted from each of the two image pickup units provided on a distal end side of the endoscope 1, that is, the first and second image pickup units 21 and 22 is transmitted to the video processor 6. On the other hand, a control signal outputted from the video processor 6 is transmitted to various kinds of component units arranged inside the operation portion 3 or on the distal end side of the insertion portion 2.

Then, the video processor 6 receives the image signals from the two image pickup units 21 and 22 described above, performs predetermined signal processing and outputs an image signal for reproduction between the processed image signals to the image display apparatus 30. Receiving the image signal for reproduction, the image display apparatus 30 continuously displays endoscopic images on its display screen.

As described above or shown in the conceptual diagram of FIG. 2, the endoscope 1 of the present embodiment configured as described above is configured having the first image pickup unit 21 in the distal end rigid portion 8 at a distal end of the insertion portion 2 as well as the second image pickup unit 22 in the bending portion 7 provided in the vicinity of the distal end portion of the insertion portion 2. In this case, the first image pickup unit 21 is configured having a first image pickup optical system capable of covering a forward field of view corresponding to a range indicated by a sign V1 in FIG. 2. Further, the second image pickup unit 22 is configured having a second image pickup optical system capable of covering a forward field of view corresponding to a range indicated by a sign V2 in FIG. 2. The second image pickup optical system is set so that the distal end of the insertion portion 2 is included within its field-of-view angle.

The conceptual diagram of FIG. 3 shows a state in a case of inserting the insertion portion 2 of the endoscope 1 in such a form, for example, into a body cavity and performing a bending operation. In FIG. 3, a tubular organ such as a large bowel in the body cavity is indicated by reference numeral 101. In a situation shown in FIG. 3, the insertion portion 2 of the endoscope 1 is inserted in the tubular organ 101, and the bending portion 7 of the insertion portion 2 is caused to bend along the tubular organ 101. Though a bending operation performed at this time is not shown, the operation is performed by the user performing a rotation operation of the angle knobs 15 while grasping the operation portion 3 shown in FIG. 1. It is assumed that, when the bending operation is performed in this way, for example, a field of vision of the first image pickup unit 21 at the distal end portion is blocked by folds and the like in the tubular organ 101. Even in such a situation, since the second image pickup unit 22 disposed in the bending portion 7 is set so that the distal end of the insertion portion 2 is included within the field-of-view angle of the second image pickup optical system, in the endoscope 1 of the present embodiment, a direction of the field of view of the second image pickup optical system follows bending of the bending portion 7, and it is possible to continuously confirm a distal end part of the insertion portion 2 and perform observation in a lumen. That is, the field-of-view direction of the second image pickup optical system is set to, when the bending portion 7 is bent, face a tangential direction of a part of the bending portion 7 to which the second image pickup optical system is attached. Therefore, the field-of-view directions of the first and second image pickup optical systems differ from each other when a bending operation is performed, and, thus, a configuration is made so that observation can be performed for a wider field of view.

Here, a specific configuration example of an internal configuration in the vicinity of the distal end portion of the endoscope 1 of the present embodiment will be described below with use of FIG. 4. Note that, in FIG. 4, only component portions related to the present invention are shown, and other component members are not shown, in order to avoid complication of the drawing. As for the other component members not shown, it is assumed that ordinary component members applied to conventional endoscopes are applied.

As described above and as shown in FIG. 4, the first image pickup unit 21 is included inside the distal end rigid portion 8 of the endoscope 1. The first image pickup unit 21 is configured with a first image pickup device 21a, a first image pickup optical system 21b, a first observation window 21c, a first image pickup cable 21f, a first holding frame 21e and the like. The first holding frame 21e is a holding member configured to hold each component member of the first image pickup unit 21 described above.

The first image pickup device 21a is a photoelectric conversion device configured to receive an optical image of a subject formed by the first image pickup optical system 21b in response to receiving an incident light flux transmitted through the first observation window 21c, and perform photoelectric conversion to generate an electrical image signal. The first image pickup cable 21f extends backward from the first image pickup device 21a. The first image pickup cable 21f is connected to the video processor 6 via the insertion portion 2, the operation portion 3, the coupling cord 4, the connector 17, the connection cord 18 and the distal end connector 19.

As described above, the first image pickup optical system 21b is an optical system for causing a subject image to be formed on a light receiving surface of the first image pickup device 21a. The first image pickup optical system 21b is disposed facing a front face of the insertion portion 2, and its optical axis O1 is set to be substantially parallel to an insertion axis of the insertion portion 2.

On the other hand, the second image pickup unit 22 is a part integrally formed so as to project outward from a predetermined part on the outer circumferential face of the bending portion 7. Each component member of the second image pickup unit 22 is held by a second holding frame 22e which is a holding member. The second image pickup unit 22 is configured mainly with a second image pickup device 22a, a second image pickup optical system 22b, a second observation window 22c, a reflecting mirror 22d, a second image pickup cable 22f, and the like.

The second image pickup device 22a is a photoelectric conversion device configured to receive an optical image of a subject for which an optical axis O2 is bent by the reflecting mirror 22d after the optical image is formed by the second image pickup optical system 22b in response to receiving an incident light flux transmitted through the second observation window 22c, and perform photoelectric conversion to generate an electrical image signal. The second image pickup cable 22f extends backward from the second image pickup device 22a. The second image pickup cable 22f is connected to the video processor 6 via the insertion portion 2, the operation portion 3, the coupling cord 4, the connector 17, the connection cord 18 and the distal end connector 19 quite similarly to the first image pickup cable 21f described above.

As described above, the second image pickup optical system 22b is an optical system for causing a subject image to be formed on a light receiving surface of the second image pickup device 22a. The second image pickup optical system 22b is disposed facing substantially the front of the insertion portion 2, and its optical axis O2 is disposed so as to be substantially parallel to or have a slight angle (more specifically, a slight angle in a direction apart from the optical axis O1) relative to the optical axis O1 of the first image pickup optical system 21b described above. FIG. 4 shows an example in which the optical axis O1 of the first image pickup optical system 21b and the optical axis O2 of the second image pickup optical system 22b are set to be substantially parallel to each other. That is, a configuration is made so that, when the insertion portion 2 is not bent, the field-of-view direction of the second image pickup optical system 22b is substantially parallel to an extending direction of the insertion portion 2.

Further, the second image pickup optical system 22b is set to, when the insertion portion 2 is bent, face a field-of-view direction different from that of the first image pickup optical system 21b.

Note that the setting of the field-of-view direction of the second image pickup optical system 22b is not limited to the shown example. For example, when the insertion portion 2 is not bent, the field-of-view direction of the second image pickup optical system 22b may be deviated from the extending direction of the insertion portion 2 by a predetermined angle. In this case, it is desirable that the deviation of the field-of-view direction is an angle within about 90 degrees in a direction apart from an axis line relative to the extending direction of the insertion portion 2 (an axial direction of the insertion portion 2).

In rear of the second image pickup optical system 22b, the reflecting mirror 22d configured to, in response to receiving a light flux which enters the second image pickup optical system 22b and travels backward and parallel to the optical axis O2, bend its optical path by about 90 degrees downwardly is disposed. The reflecting mirror 22d is disposed being pasted, for example, on an inclined inner surface of the second holding frame 22e. In this case, the inclined surface to which the reflecting mirror 22d is attached is set to have an angle of about 45 degrees relative to the optical axis O2. An image of the light flux (a subject image) which has been folded by the reflecting mirror 22d described above is formed on an image pickup surface of the second image pickup device 22a. For this reason, the second image pickup device 22a is disposed, for example, so that the image pickup surface is substantially parallel to an insertion direction of the insertion portion 2 (a direction along the optical axes O1 and O2).

Due to the configuration, (the) image signals acquired by the two image pickup units 21 and 22, respectively, are transmitted to the video processor 6 described above, receive various kinds of signal processing, and are displayed as continuous video (a movie) by the image display apparatus 30 in the end.

Note that the bending portion 7 of the endoscope 1 is configured with an ordinary bending mechanism configured with a plurality of bending pieces 7a which are connectedly arranged, so as to be bendable. It is assumed that other components are similar to those of a conventional endoscope though they are not shown.

As described above, according to the first embodiment described above, a configuration is made by providing an image pickup unit similar to that applied in a conventional endoscope, that is, the first image pickup unit 21 including the first image pickup optical system 21b in the distal end rigid portion 8 disposed at the distal end of the insertion portion 2 of the endoscope 1 similarly to a conventional endoscope, as well as disposing the second image pickup unit 22 including the second image pickup optical system 22b on the outer circumferential face of the bending portion 7 provided in the vicinity of the distal end portion of the insertion portion 2 and bendingly operated by a proximal side operation. In this case, the configuration is made so that the distal end (the distal end rigid portion 8) of the insertion portion 2 is included within the field-of-view angle of the second image pickup optical system 22b of the second image pickup unit 22 described above. Due to the configuration, either when the endoscope 1 is bent or not bent, it does not happen in the endoscope system of the present embodiment that sight of the distal end part of the insertion portion 2 is lost by the second image pickup optical system 22b (the second image pickup unit 22). Further, even if an observation field of view by the first image pickup optical system 21b (the first image pickup unit 21) on the distal end side is blocked, for example, by folds of a large bowel, it is possible to continuously observe an inside of a lumen of the large bowel using the second image pickup optical system 22b (the second image pickup unit 22).

Second Embodiment

In the first embodiment described above, a configuration is made so that the distal end rigid portion 8 of the endoscope 1 is included within the field-of-view angle of the second image pickup optical system 22b of the second image pickup unit 22 by disposing the second image pickup unit 22 including the second image pickup optical system 22b at a predetermined part on the outer circumferential face of the bending portion 7 of the insertion portion 2 of the endoscope 1. In this case, in the endoscope 1 in the endoscope system of the first embodiment described above, the second image pickup unit 22 including the second image pickup optical system 22b is configured being integrally provided inside the insertion portion 2 of the endoscope 1. The present invention is not limited to such a form. For example, a configuration like a second embodiment shown below is also conceivable.

Figure 5:
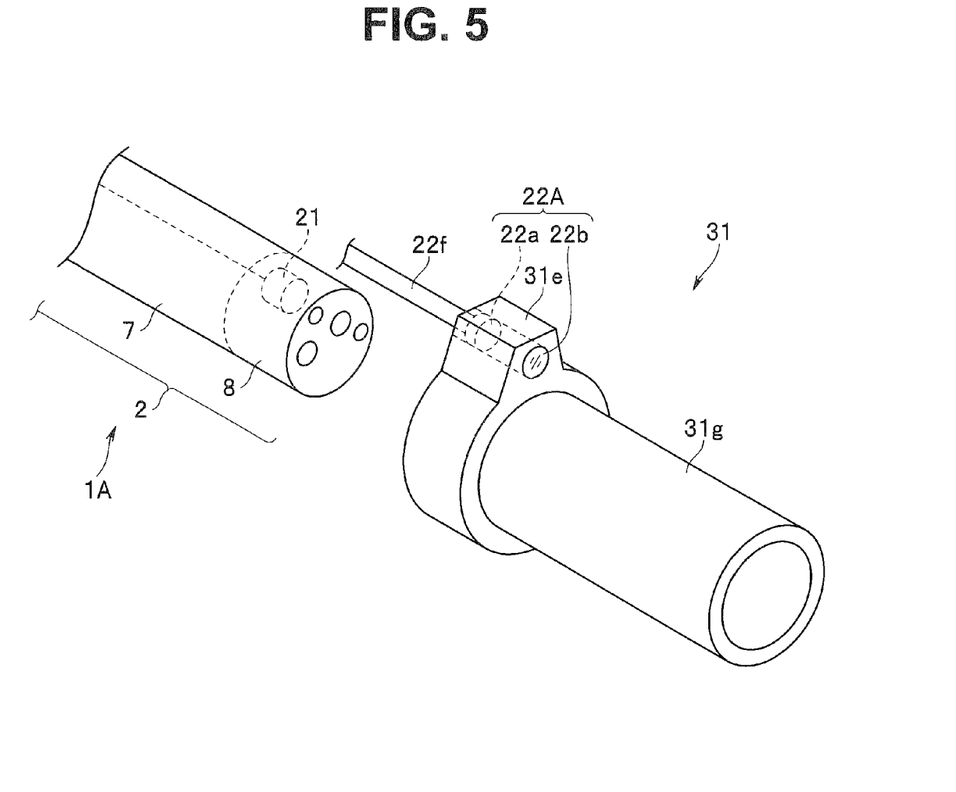
FIG. 5 is a schematic perspective view showing a configuration in a vicinity of a distal end portion of an endoscope in an endoscope system of a second embodiment of the present invention.

FIG. 5 is a schematic perspective view showing a configuration in a vicinity of a distal end portion of an endoscope in an endoscope system of the second embodiment of the present invention. Note that, in FIG. 5, other component members similar to those of the first embodiment described above are not shown and described being given same reference numerals.

Though a basic configuration of the present embodiment is substantially similar to that of the first embodiment described above, the present embodiment is different in a point that a configuration is made in which, in addition to an endoscope in an ordinary form, a second image pickup unit including a second image pickup optical system is provided on a distal end cover member configured as a separate body, and the endoscope in a form of the distal end cover member being fixed to the endoscope is adopted as an endoscope. In this case, the second image pickup unit including the second image pickup optical system, which is provided on the distal end cover member, is similar to the first embodiment described above in a point that it is disposed at a predetermined part on an outer circumferential face of a bending portion of an insertion portion of the endoscope. Due to the configuration, a distal end rigid portion of the endoscope is configured so as to be included within a field-of-view angle of the second image pickup optical system of the second image pickup unit.

In the endoscope system of the present embodiment, an endoscope is configured including an endoscope 1A substantially similar to a conventional endoscope with a common configuration, and the distal end cover member covering a vicinity of a distal end portion of the endoscope 1A.

In the endoscope system of the present embodiment, an endoscope having a configuration similar to that of a conventional ordinary endoscope is applied as the endoscope 1A itself. An insertion portion 2 of the endoscope 1A is configured with a flexible tube 9 (not shown in FIG. 5), a bending portion 7 and a distal end rigid portion 8, which are connectedly arranged in that order from an operation portion 3 (not shown) side, that is, from a proximal end portion side. Inside the distal end rigid portion 8, a first image pickup unit 21 which covers a forward field of view is included. The first image pickup unit 21 has a configuration substantially similar to that of the endoscope 1 of the first embodiment described above or an image pickup unit which has been commonly spread conventionally in a point that it is configured, for example, with a first image pickup optical system, an image pickup device and the like.

A distal end cover member 31 is configured so as to be able to cover the vicinity of the distal end portion of the endoscope 1A, and it is a component member formed in a substantially cylindrical shape as a whole. The distal end cover member 31 is configured so as to be attachable to and detachable from a distal end part of the insertion portion 2 of the endoscope 1A.

The distal end cover member 31 is disposed on a distal end side and is configured mainly with a cylindrical portion 31g which covers an area from the distal end rigid portion 8 to a part of the bending portion 7 in the vicinity of the distal end portion of the endoscope 1A, and a projection-shaped portion 31e formed on an outer circumferential face of a proximal end edge portion of the cylindrical portion 31g and disposed projecting outward.

The cylindrical portion 31g of the distal end cover member 31 is formed so that an inner diameter is slightly larger than an outermost diameter of the endoscope 1A, and an opening is formed at each of both ends in a longitudinal axis direction. An opening on a proximal end side is an insertion port through which the endoscope 1A is to be inserted. An opening on a distal end side is set so as to be smaller than a diameter of the distal end edge portion of the endoscope 1A so that a distal end face of the endoscope 1A insertedly disposed in the distal end cover member 31 does not project in the longitudinal axis direction.

A second image pickup unit 22A is included inside the projection-shaped portion 31e on the proximal end side of the cylindrical portion 31g described above. The second image pickup unit 22A is configured with a second image pickup device 22a, a second image pickup optical system 22b, a second image pickup cable 22f and the like.

Due to such a configuration, when the distal end cover member 31 described above is fitted to the distal end part of the endoscope 1A, the second image pickup unit 22A including the second image pickup optical system 22b is disposed at a predetermined position in a form of the distal end rigid portion 8 of and a part of the bending portion 7 of the endoscope 1A being covered with the cylindrical portion 31g. In this case, the second image pickup optical system 22b (the second image pickup unit 22A) is disposed in the bending portion 7 provided in the vicinity of the distal end portion of the insertion portion 2 and bendingly operated by a proximal side operation, and configured so that a distal end of the insertion portion 2 is included within the field-of-view angle.

Note that a video processor 6 of the present embodiment is configured to be able to receive image signals from the two image pickup units 21 and 22A described above and appropriately perform processing, similarly to the first embodiment described above. Other components are substantially similar to those of the first embodiment described above.

In the endoscope system of the present embodiment configured as described above, operation in a case of inserting the endoscope 1A, for example, into a body cavity and performing a bending operation in a state that the distal end cover member 31 is fitted to the endoscope 1A is substantially similar to the case of the first embodiment described above.

As described above, according to the second embodiment described above, since the distal end cover member 31 configured to be attachable to and detachable from the distal end part of the endoscope 1A is provided with the second image pickup unit 22A, it is possible to obtain an advantageous effect similar to that of the first embodiment described above only by fitting the distal end cover member 31 to the endoscope 1A having a conventional common configuration.

Note that the present invention is not limited to the embodiments described above, and it is, of course, possible to perform various modifications and applications within a range not departing from the spirit of the invention. Furthermore, the embodiments described above include inventions at various stages, and the various inventions can be extracted by appropriate combinations of a plurality of constituent features disclosed. For example, even if some constituent features are deleted from all constituent features shown in one of the embodiments described above, a configuration obtained after deleting the constituent features can be extracted as an invention if the problem to be solved by the invention can be solved, and the advantageous effect of the invention can be obtained. Furthermore, components of different embodiments may be appropriately combined.

INDUSTRIAL APPLICABILITY

The present invention can be applied not only to an endoscope and an endoscope system in the medical field but also to an endoscope and an endoscope system in the industrial field.

What is claimed is:

1. An endoscope comprising:
a first image pickup optical system provided at a distal end of an insertion portion;
a bending portion provided in a vicinity of a distal end portion of the insertion portion and configured to be bendingly operated by a proximal side operation; and
a second image pickup optical system disposed on the bending portion, the second image pickup optical system being configured so that the distal end of the insertion portion is included within a field-of-view angle of the second image pickup optical system;
wherein, when the bending portion is in a non-bending state, an optical axis of the first image pickup optical system is fixed to be substantially parallel to an optical axis of the second image pickup optical system.

2. The endoscope according to claim 1, wherein the second image pickup optical system is provided inside the insertion portion of the endoscope.

3. The endoscope according to claim 2, wherein, when the bending portion is in a non-bending state, a field-of-view direction of the second image pickup optical system is substantially parallel to an extending direction of the insertion portion.

4. The endoscope according to claim 2, wherein, when the bending portion is in the non-bending state, the field-of-view direction of the second image pickup optical system is deviated from the extending direction of the insertion portion by a predetermined angle.

5. The endoscope according to claim 1, wherein the second image pickup optical system is configured to be attachable to and detachable from the insertion portion of the endoscope.

6. The endoscope according to claim 5, wherein, when the bending portion is in a non-bending state, a field-of-view direction of the second image pickup optical system is substantially parallel to an extending direction of the insertion portion.

7. The endoscope according to claim 5, wherein, when the bending portion is in the non-bending state, the field-of-view direction of the second image pickup optical system is deviated from the extending direction of the insertion portion by a predetermined angle.

8. The endoscope according to claim 1, wherein the second image pickup optical system faces a field-of-view direction different from a field-of-view direction of the first image pickup optical system when the bending portion is bent.

9. An endoscope system comprising:
an endoscope comprising:
a first image pickup unit including a first image pickup optical system and a first image pickup device, the first image pickup unit being provided at a distal end of an insertion portion;
a bending portion provided in a vicinity of a distal end portion of the insertion portion and configured to be bendingly operated by a proximal side operation; and
a second image pickup unit disposed on the bending portion the second image pickup unit including a second image pickup optical system and a second image pickup device, wherein the second image pickup optical system is configured so that the distal end of the insertion portion is included within a field-of-view angle of the second image pickup optical system, wherein, when the bending portion is in a non-bending state, an optical axis of the first image pickup optical system is fixed to be substantially parallel to an optical axis of the second image pickup optical system;
an image processing control apparatus configured to receive image signals from the first image pickup unit and the second image pickup unit and perform image processing, and control the first image pickup unit and the second image pickup unit; and
an image display apparatus configured to receive an image signal outputted from the image processing control apparatus and display an image.

10. An endoscope comprising:
a first image pickup optical system provided at a distal end of an insertion portion;
a bending portion provided in a vicinity of a distal end portion of the insertion portion and configured to be bendingly operated by a proximal side operation; and
a second image pickup optical system fixed at a predetermined position on the bending portion, the second image pickup optical system being configured at the predetermined position such that the distal end of the insertion portion is included within a field-of-view angle of the second image pickup optical system whether the bending portion is in an unbent state or in a bent state.

* * * * *